United States Patent
Mathews et al.

[11] Patent Number: 5,753,185
[45] Date of Patent: May 19, 1998

[54] VEHICLE EMISSIONS TESTING SYSTEM

[75] Inventors: Loren T. Mathews; Radhakrishna Murty Neti, both of Yorba Linda, Calif.

[73] Assignee: California Analytical Instruments, Inc., Orange, Calif.

[21] Appl. No.: 636,562

[22] Filed: Apr. 23, 1996

[51] Int. Cl.$^6$ .............. G01N 31/12; G01N 30/00
[52] U.S. Cl. .............. 422/94; 422/83; 422/86; 73/23.2; 73/23.31; 436/137
[58] Field of Search .............. 73/23.2, 23.31; 422/83, 86, 94; 436/137

[56] References Cited

U.S. PATENT DOCUMENTS

| | | | |
|---|---|---|---|
| 4,040,783 | 8/1977 | Collin | 23/232 R |
| 4,193,965 | 3/1980 | Cullingford et al. | 422/95 |
| 4,981,652 | 1/1991 | Ratfisch | 123/1 A |
| 5,343,906 | 9/1994 | Tibbals | 141/83 |
| 5,367,470 | 11/1994 | Lang | 364/498 |
| 5,369,976 | 12/1994 | Ratton | 73/23.2 |
| 5,377,528 | 1/1995 | Dauvergne | 73/31.01 |
| 5,517,237 | 5/1996 | Cocanour | 348/189 |
| 5,589,629 | 12/1996 | Quinn | 73/23.31 |
| 5,592,372 | 1/1997 | Artail et al. | 364/178 |

*Primary Examiner*—Harold Y. Pyon
*Attorney, Agent, or Firm*—John E. Vanderburgh

[57] ABSTRACT

There is provided an emission testing system which maintains system integrity and which can be manufactured at less cost than current standard emission testing systems. The system includes a sampling unit for collecting emissions from a vehicle and diluting the collected emissions with background ambient air as required and means for drawing a proportional test sample from the bulk air/emission mixture. The analyzer is a single unit which includes a reaction cell for chemiluminescence reactions and a combustion cell for flame ionization analysis. In addition the system includes a common sample conditioning for the test sample prior to splitting the test sample for chemiluminescence and flame ionization analysis.

5 Claims, 2 Drawing Sheets

VEHICLE EMISSIONS TESTING SYSTEM

BACKGROUND OF THE INVENTION

Vehicle emission testing is widely practiced as one phase of the efforts to reduce air pollution. The products of internal combustion of fossil fuels in gasoline or diesel powered engines includes unburned hydrocarbons, oxygenated organic compounds, carbon monoxide, carbon dioxide, moisture and oxides of nitrogen. Conventionally, these exhaust emission compounds are measured with separate flame ionization analyzers for the determination of unburned hydrocarbons, and infrared analysis for the determination of carbon monoxide and carbon dioxide and chemiluminescence techniques employed for the analysis of the oxides of nitrogen. With the exception of infra- red, these techniques are conventionally employed in vehicle emission testing systems employed for the routine inspection of emissions by motor vehicles.

In vehicle emission testing, the presence of moisture in the sample gas is generally considered harmful because of the possible reaction between the components being tested such as oxides of nitrogen and hydrocarbons with the moisture to form by- products which are not detected by the emission testing equipment and which result in erroneous readings. Consequently each of the analyzers normally provides for removal of moisture from the test sample. Depending on the method of moisture removal, the reported level of emissions from the same sample but run through different analyzers may be different because of the differences in sample conditioning. The condition of the sample as it is led to the different analyzers is referred to as system integrity. Other factors may also be involved in system integrity in addition to the method in which the sample is handled for removal of moisture. For example differences in flow rate and travel distance to the analyzer can result in loss of system integrity as well as differences in treatment for the removal of moisture. Maintaining system integrity is important in routine vehicle emission testing procedures and is of particularly great importance for research into fuel combustion and motor emission research. In addition, with the increased demand for emission testing, it would be desirable to provide a reliable emission testing system which preserves sample integrity and which can be manufactured less expensively than current emission testing systems.

SUMMARY OF THE INVENTION

In accordance with the present invention there is provided an emission testing system which maintains system integrity and which can be manufactured at less cost than current standard emission testing systems. The system of the present invention includes a sampling unit, of any suitable design as is conventional in the art, for collecting emissions from a vehicle and diluting the collected emissions with background ambient air as required. Preferably, the sampling unit is provided with means for drawing a proportional test sample from the bulk air/emission mixture.

In accordance with the invention, the analyzer is a single unit which comprises a reaction cell for chemiluminescence reactions and a combustion cell for flame ionization analysis. In addition the system includes common sample conditioning for the test sample prior to splitting the test sample for chemiluminescence and flame ionization analysis.

In somewhat more detail, the test sample, drawn from the sample collection unit, is passed for conditioning through a dryer for the removal of moisture from the test sample. The sample then passes through a common flow restricter for controlling flow rate and pressure and thence to a splitter where the sample is split into a stream for flame ionization analysis and a stream for chemiluminescence analysis. The common flow restricter and common sample conditioning insures that sample conditioning is the same for both the portion of test sample used in the hydrocarbon determination and NO analysis thus maintaining the integrety of the sample integrity.

As mentioned above both analysis techniques are combined in a single unit and the collector of the flame ionization detector is coupled directly to an operational amplifier for amplification of the output signal. Likewise the photo diode or photo-multiplier is closely coupled to an operational amplifier for amplification of its output signal. This method allows for the elimination of expensive shielding which is normally provided in conventional analyzers and also provides for a substantial reduction in sample of path length which reduces the chances of undesired reactions in the line as the sample is led to the chemiluminescence reaction cell or the flame ionization combustion chamber.

The features and advantages of the present invention will be more apparent from a reading of the following detailed description of the invention taken in conjunction with the drawings.

DETAILED DESCRIPTION OF THE INVENTION

Figure 1:
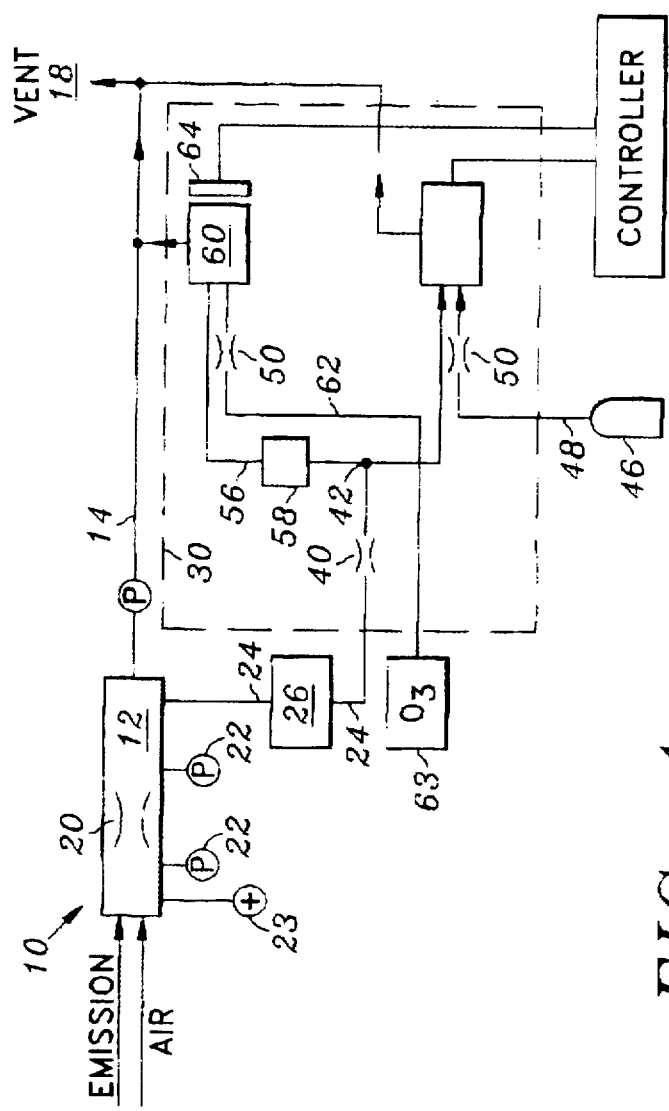
FIG. 1 is a block diagram of the analysis system in accordance with the present invention.

Referring to FIG. 1, the system 10 of the present invention includes a sample collection unit 12 which functions to collect emission samples from a vehicle and provide dilution background air to the sample. Various designs of sample collection units 12 are currently commercially available and do not, per se, form a part of the present invention. The sample collection unit 12 is vented through a line 14. As shown, a pump 16 in the line 14 moves the bulk air and emission mixture through the system 10 to vent 18. The sample collector unit 12 illustrated includes a flow restricter 20, such as for example a square edge orifice, and upstream and downstream pressure sensing devices 22 for regulating and sensing the bulk flow through the sample collection unit 12. Temperature sensing means 23 may also be included as well as a controller for receiving signals from the temperature and pressure sensing units and for calculating and recording the temperature and bulk flow through the sample collection unit 12. Sample collection units 12 of the general type described herein are manufactured and sold by California Analytical Instruments, Inc. Orange Calif. under the trade name RG240. Means are provided in the sample collection unit for controllably extracting a test sample for analysis.

The extracted test sample is led through a line 24 to a dryer 26 for conditioning by the removal of a substantial portion of moisture which is contained in the sample. It is important in the analysis NO by chemiluminescence to remove excess moisture from the sample since moisture may act to quench the light output from the chemiluminescence reaction. Likewise moisture can react with the NOx components to produce erroneous quantitative results. Thus, when running analysis of a sample for several components, such as hydrocarbons, CO, CO2 and NOx, it has been necessary to use different analyzers for the different components. Each analyzer is equipped with its own sample conditioning equipment. When the samples are conditioned in different dryers or dried to different levels of moisture content, the results of the reactions may be biased and the relative proportions of hydrocarbons, CO, CO2 and NOx in the sample will be incorrect. Moisture may be removed from the test sample in the dryer 26 by various methods including heating the test sample, cooling it to lower its dew point or by passing the test sample through a suitable desiccant.

The conditioned test sample is carried by a line 24 to the analyzer 30 for analysis of the selected components, i.e. NOx, CO, $CO_2$, and a total uncombusted hydrocarbon. The analyzer 30 is adapted for both flame ionization and chemiluminescence techniques. Both of the analysis methods are contained in a common housing and employ a common flow restricter 40 through which the test sample from the dryer 26 passes before reaching the splitter 42 for division of the test sample stream. A line 28 carries one stream of test sample to the flame ionization detection cell 32 where it is mixed with a suitable fuel, such as hydrogen or hydrogen/inert gas mixture prior to ignition in the ignition cell. The flame ionization detection cell 32 operates in a conventional fashion, that is upon ignition the sought after substance is ionized and collected on a positively charged collector which creates an ionic current the strength of which is proportional to the quantity of the sought for substance in the sample gas. The fuel is contained in pressurized tanks and led through a line 48 and flow restricter 50 to the sample line 28 for admixture with the sample gas. A preferred fuel is a mixture of hydrogen and helium (40% hydrogen/60% helium). Suitable valves (not shown) can be provided in the line for regulating and shutting off the flow of fuel to the sample line. Hydrogen free air is also introduced to the burner through a line 52. Ignition in the burner assembly of the flame ionization detection cell 32 may be by glow plug or heated wire, which may also may serve as the collector for the ionized sample. The construction and operation of the flame ionization detection cell 32 is well understood in the art and, as stated below, does not form a part of the present invention.

A line 56 leads the second stream of test sample from the splitter 42 through a converter 58 for the conversion of NOx to NO and thence to the chemiluminescence reaction cell 60 for reaction with ozone which is introduced to the reaction cell through a line 62 from a source of ozone 63. The reaction between NO and ozone produces light as a by-product, the intensity of which is directly related to the concentration of NO in the test sample. A suitable photo detector 64, such as a solid state photo diode or photo multiplier tube senses the intensity of the light and produces a signal which is directly related to the intensity of the light.

Chemiluminescence determinations are often run with negative pressure in the reaction cell. In accordance with the invention, however, the chemiluminescence reaction cell 36 is maintained at ambient or slight positive pressure to essentially match the pressure in the combustion chamber of the flame ionization detection cell 34. In this manner the integrity of the sample in the analyzer 30 is maintained because sample to the flame ionization detection cell 32 and the chemiluminescence reaction cell 36 is conditioned in the same way.

The signal from the flame ionization detection cell 32 and from the photo detector 64 of the chemiluminescence reaction cell 36 are passed through conventional amplification circuitry which includes an operational amplifier 65 to a recorder 66 for recording and display. Best results are achieved by coupling the burner collector of the flame ionization detection cell 32 directly to the operational amplifier input. Likewise the photo detector 64 of the chemiluminescence reaction cell 36 is closely coupled with its operational amplifier 65. This approach provides an improved signal from both detectors, both in strength and in precision and reduces the cost of the analyzer 30 by eliminating costly shielding which is normally required to prevent background noise from overwhelming the signal from the detectors.

In addition to the foregoing other advantages are achieved by combining the flame ionization detection cell 32 and the chemiluminescence cell 36 in a single housing 31. For example the path through which the sample gas must travel is substantially reduced thus minimizing transport time and reducing the opportunity for the loss through reaction with contaminants of sought for components during transport from the collection unit 12 to the analyzer 30.

EXAMPLE

To demonstrate the accuracy and reliability of the emission system 10 of the present invention, the system 10 was installed in a vehicle test station and the vehicle emissions of 200 automobiles were tested for NO and for total hydrocarbons. The results were compared to those obtained using a standard prior art emission testing system which employs separate analyzers for the analysis of NO and total hydrocarbons. This system was manufactured and sold by Marta Technologies Inc. and identified as the IM-240 system.

The test procedure was in conformance with the California BAR Test Procedure No. 90. In accordance with that procedure, the system 10 of the present invention was run in series with the IM240 system and duplicate test samples were drawn from a common sample collection unit 12 of the type described above. The test samples were taken at essentially the same time.

The test sample for analysis by the MARTA System was divided into two streams; one stream being sent to the separate flame ionization analyzer and the other stream being sent to the separate chemiluminescence analyzer. The streams were subjected to conditioning and drying at each of the analyzers. The sample drawn for the system 10 of the present invention was passed through the common dryer 26 and flow restricter 40 and thence to the analyzer 30 where it was divided by the splitter 42 into two streams for determination of hydrocarbons by flame ionization and for the oxides of nitrogen by chemiluminescence reaction of the sample with ozone.

The test protocols at the flame ionization analyzer was the same for the MARTA and the system 10 of the present invention and both flame ionization detectors utilize the same hydrogen/nitrogen fuel. The sample flow rate to the MARTA System was 700 cfm as per the manufacturer's instructions and the flow rate to the system 10 of the present invention was maintained between 250 and 300 CFM.

The comparative test results for total hydrocarbons CO, $CO_2$ and oxides of nitrogen obtained from 12 randomly selected vehicles are set forth in the tables A and B below. The comparative results of the total hydrocarbon and oxides of nitrogen determinations and are plotted as bar graphs in FIGS. 2 and 3 respectively. As can be seen from the tables and from FIGS. 2 and 3, excellent correlation and results using the system of the present invention and the MARTA System have been achieved.

Figure 2:
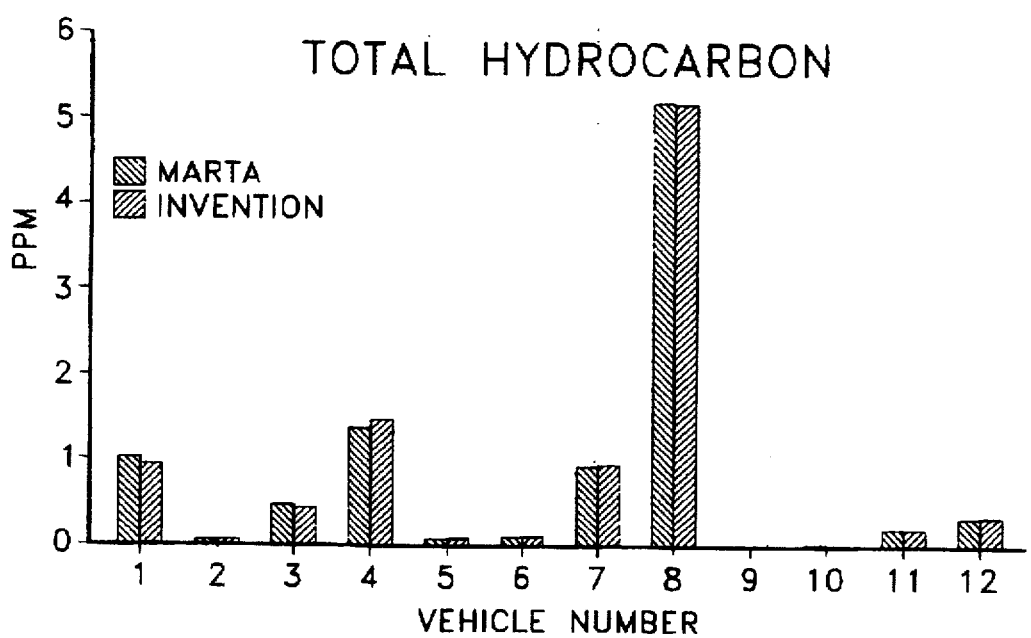
FIG. 2 is a bar graph comparing the test results for hydrocarbon determinations obtained using the system of the present invention and a prior art vehicle emission testing system.
Figure 3:
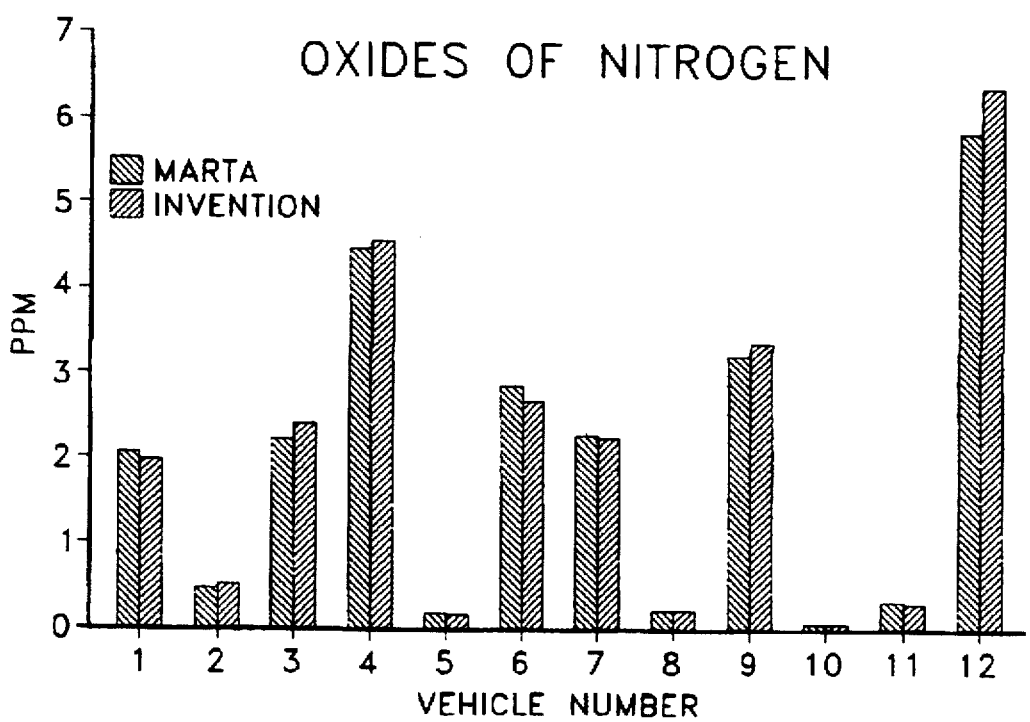
FIG. 3 is a bar graph comparing the test results for NOX determinations obtained using the system of the present invention and a prior art vehicle emission testing system.

FIG. 2 is a bar graph comparing the results obtained in NO testing between the MARTA System and the system 10 of the present invention. Likewise FIG. 3 is a bar graph showing the comparative results for total hydrocarbons. As can be seen the correlation between the MARTA system and the present invention is very close.

TABLE A

MARTA SYSTEM/ Results as ppm

| Veh # | HC* | CO | NO | CO$_2$ |
|---|---|---|---|---|
| 1 | 1.019 | 07.683 | 2.058 | 795.799 |
| 2 | 0.059 | 14.100 | 0.470 | 383.768 |
| 3 | 0.470 | 02.400 | 2.215 | 342.000 |
| 4 | 1.372 | 23.520 | 4.469 | 591.763 |
| 5 | 0.078 | 13.670 | 0.176 | 304.000 |
| 6 | 0.098 | 05.272 | 2.842 | 561.089 |
| 7 | 0.921 | 03.490 | 2.260 | 408.000 |
| 8 | 5.174 | 06.740 | 0.216 | 345.000 |
| 9 | 8.036 | 14.170 | 3.214 | 273.000 |
| 10 | 0.020 | 09.220 | 0.059 | 550.000 |
| 11 | 0.196 | 07.252 | 0.314 | 670.614 |
| 12 | 0.333 | 11.074 | 5.841 | 690.155 |

*Unburned hydrocarbons

TABLE B

SYSTEM OF THE INVENTION/ Results as ppm

| Veh # | HC* | CO | NO | CO$_2$ |
|---|---|---|---|---|
| 1 | 0.939 | 08.133 | 1.978 | 816.799 |
| 2 | 0.064 | 12.000 | 0.510 | 369.768 |
| 3 | 0.434 | 02.170 | 2.405 | 334.000 |
| 4 | 1.472 | 20.220 | 4.559 | 576.763 |
| 5 | 0.080 | 12.170 | 0.169 | 314.000 |
| 6 | 0.104 | 05.082 | 2.662 | 548.089 |
| 7 | 0.945 | 03.220 | 2.230 | 412.000 |
| 8 | 5.164 | 05.840 | 0.217 | 355.000 |
| 9 | *62.220 | 16.170 | 3.354 | 263.000 |
| 10 | 0.019 | 10.400 | 0.063 | 552.000 |
| 11 | 0.188 | 6.602 | 0.291 | 691.614 |
| 12 | 0.341 | 12.574 | 6.381 | 660.155 |

From the foregoing it can be seen that the system of the present invention provides a reliable system for testing NO and total hydrocarbons in vehicle emissions using a single analyzer which is adapted for chemiluminescence and flame ionization detection techniques. The system of the invention produces results which are essentially the same as those obtained using the more expensive MARTA system.

The system of the invention provides an instrument which is designed to provide the advantages of the MARTA system are less cost thus making the quality emissions testing of the MARTA system available for small emissions testing facilities and at less cost. For example, by combining the two testing techniques in a single unit, travel time for the sample through the analyzer is substantially reduced. By utilization of a single dryer, flow restricter and splitter, the uniformity of samples going to the chemiluminescence reaction cell and the flame ionization combustion cell is assured. In this manner the sample is uniformly conditioned and passed at a uniform flow rate to the chemiluminescence and flame ionization analysis areas. Combining the two analytical protocols in a single unit and coupling the output of each detectors to an operational amplifier allows for the elimination of expensive shielding and results in a highly reliable emission testing unit which can be produced at a lower cost than the conventional units currently in use for vehicle emission testing.

As will be understood by those skilled in the art, various arrangements which lie within the spirit and scope of the invention other than those described in detail in the specification will occur to those persons. It is therefore to be understood that the invention is to be limited only by the claims appended hereto.

Having described the invention, we claim:

1. In an emission testing system including means for collecting vehicle emissions, means for drawing a test sample of said collected vehicle emission for the determination of pollutant components, and analyzer means for determining said pollutant components, the improvement comprising:

said analyzer means consisting of a single unit including a housing in which is disposed a chemiluminescence reaction cell and a flame ionization detection cell;

common means for conditioning said test sample to lower the moisture content thereof prior to said conditioned test sample reaching said analyzer means;

common means for controlling the flow rate and pressure of said conditioned test sample; and splitter means for dividing said conditioned test sample to provide uniform conditioned sample flow to said chemiluminescence reaction cell and said flame ionization detection cell.

2. The emission testing system of claim 1 wherein pressure in said chemiluminescence reaction cell is at least ambient.

3. The emission testing system of claim 1 wherein pressure in said chemiluminescence reaction cell is substantially equal to pressure in said flame ionization detection cell.

4. The emission testing system of claim 1 further including means for recording and displaying the signal output from said chemiluminescence reaction cell and said flame ionization detection cell, said means including amplification circuitry having an operational amplifier and associated circuitry for amplifying said output signals from each of said flame ionization detection cell and said chemiluminescence reaction cell, said flame ionization detection cell including a collector for ionized sample, said collector being coupled directly to a corresponding operational amplifier and said chemiluminescence reaction cell including a photo detector, said photo detector being coupled directly to a corresponding operational amplifier.

5. The emission testing system of claim 1 wherein said common means for controlling the flow rate and pressure of said conditioned test sample consists of a flow restricter in a line carrying said test sample to said analyzer means, said flow restrictor being located in said line between said dryer and said analyzer means thereby to control the pressure and flow rate of said conditioned sample to said analyzer.

* * * * *